United States Patent
Morishima et al.

(10) Patent No.: US 10,203,346 B2
(45) Date of Patent: Feb. 12, 2019

(54) AUTOMATIC ANALYSIS DEVICE

(71) Applicant: Hitachi High-Technologies Corporation, Minato-ku, Tokyo (JP)

(72) Inventors: Daisuke Morishima, Tokyo (JP); Kohshi Maeda, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 3 days.

(21) Appl. No.: 15/028,807

(22) PCT Filed: Oct. 21, 2014

(86) PCT No.: PCT/JP2014/077998
§ 371 (c)(1),
(2) Date: Apr. 12, 2016

(87) PCT Pub. No.: WO2015/060316
PCT Pub. Date: Apr. 30, 2015

(65) Prior Publication Data
US 2016/0238624 A1 Aug. 18, 2016

(30) Foreign Application Priority Data
Oct. 22, 2013 (JP) .................. 2013-219490

(51) Int. Cl.
*G01N 35/00* (2006.01)
*G01N 35/10* (2006.01)
*C12Q 1/6813* (2018.01)

(52) U.S. Cl.
CPC ..... *G01N 35/00594* (2013.01); *C12Q 1/6813* (2013.01); *G01N 35/00663* (2013.01);
(Continued)

(58) Field of Classification Search
None
See application file for complete search history.

(56) References Cited

U.S. PATENT DOCUMENTS

| | | |
|---|---|---|
| 2006/0120921 A1 | 6/2006 | Elliot et al. |
| 2010/0191382 A1 | 7/2010 | Samuhel et al. |

(Continued)

FOREIGN PATENT DOCUMENTS

| | | |
|---|---|---|
| JP | 2004-129620 A | 4/2004 |
| JP | 2006-521542 A | 9/2006 |

(Continued)

OTHER PUBLICATIONS

International Search Report (PCT/ISA/210) issued in PCT Application No. PCT/JP2014/077998 dated Jan. 27, 2015 with English translation (5 pages).

(Continued)

*Primary Examiner* — Kathryn Wright
(74) *Attorney, Agent, or Firm* — Crowell & Moring LLP

(57) ABSTRACT

Provided is an automatic analysis device capable of reducing a reagent cost. In the present invention, in each mixed reagent preparation cycle, an amount of mixed reagent for N analyses is mixed and prepared, and an amount of mixed reagent for one analysis is dispensed from the amount of mixed reagent for N analyses and used to analyze one sample. Minimum (Nmin) and maximum (Nmax) values for N are determined for a control unit beforehand, and if the analysis of J samples is requested, the control unit sets the value of N at the time of a mixed reagent preparation cycle within a range from Nmin to Nmax so as to minimize the remaining mixed reagent.

10 Claims, 14 Drawing Sheets

(52) U.S. Cl.
CPC ... *G01N 35/1002* (2013.01); *G01N 35/00693* (2013.01); *G01N 2035/00673* (2013.01); *G01N 2035/1034* (2013.01)

(56) References Cited

U.S. PATENT DOCUMENTS

| | | | |
|---|---|---|---|
| 2012/0275956 A1* | 11/2012 | Wakamiya | G01N 35/00663 422/68.1 |
| 2013/0084213 A1* | 4/2013 | Nishikawa | G01N 35/00712 422/73 |
| 2013/0121882 A1 | 5/2013 | Kimura et al. | |

FOREIGN PATENT DOCUMENTS

| | | |
|---|---|---|
| JP | 2012-32190 A | 2/2012 |
| JP | 2012-55271 A | 3/2012 |
| JP | 2013-134069 A | 7/2013 |

OTHER PUBLICATIONS

Japanese-language Written Opinion (PCT/ISA/237) issued in PCT Application No. PCT/JP2014/077998 dated Jan. 27, 2015 (3 pages).
Japanese-language Request for International Preliminary Examination Report (PCT/IPEA/401) and International Preliminary Examination Report on Patent Ability (Chapter II) (PCT/IPEA/ 409) issued in PCT Application No. PCT/JP2014/077998 dated Jan. 1, 2016 (13 pages).

\* cited by examiner

[Fig. 1]
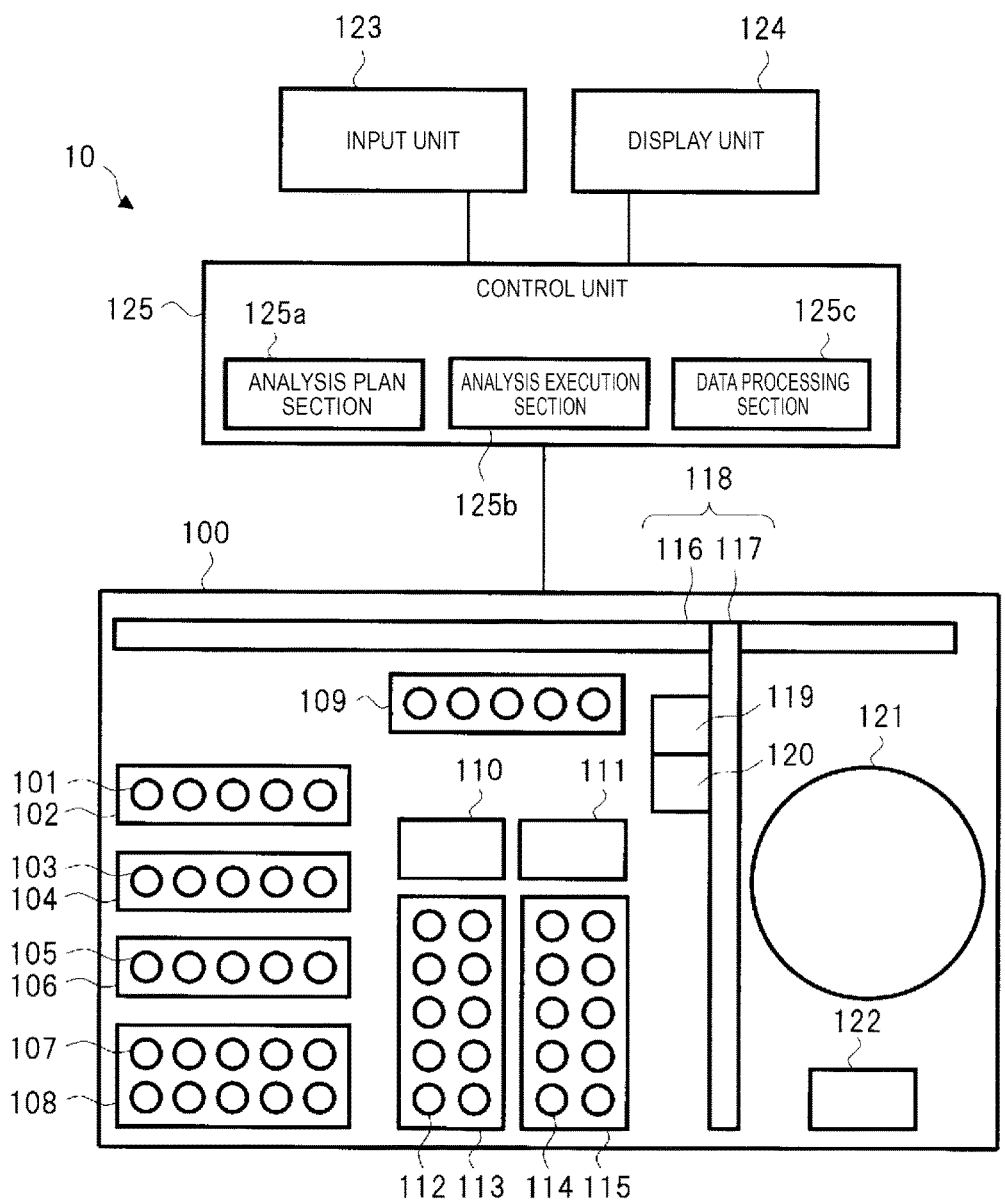

[Fig. 2]
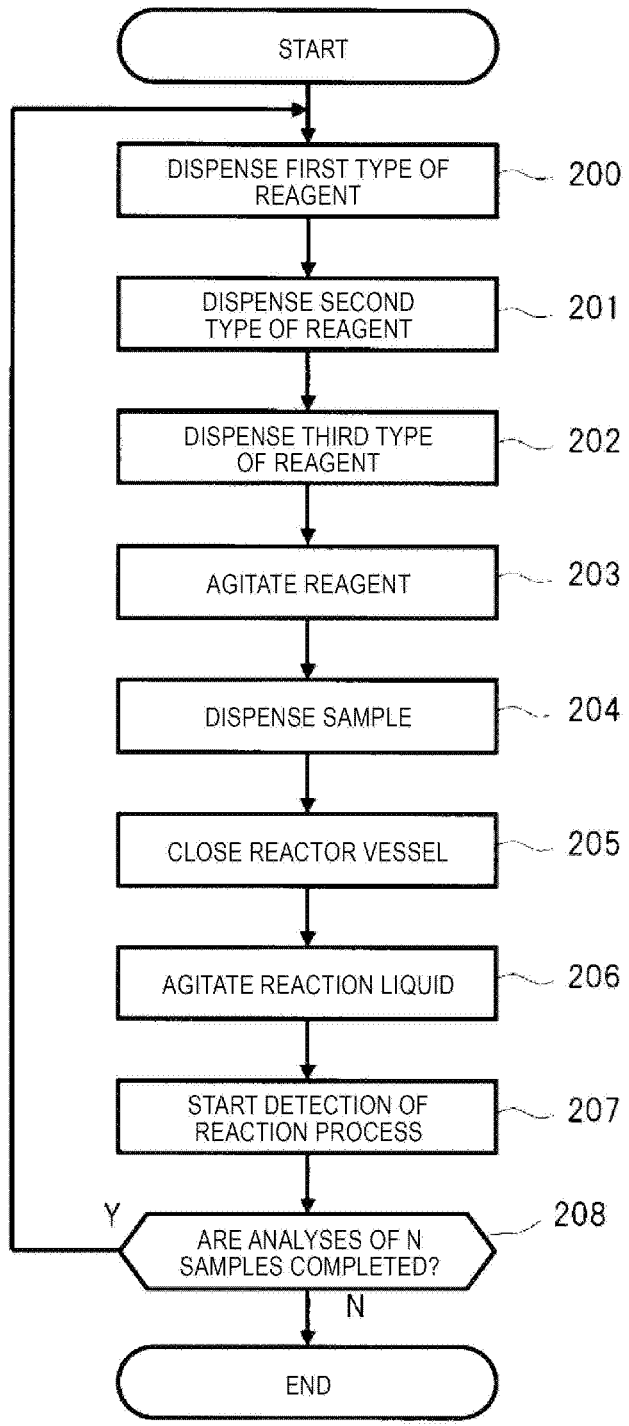
Prior Art

[Fig. 3]
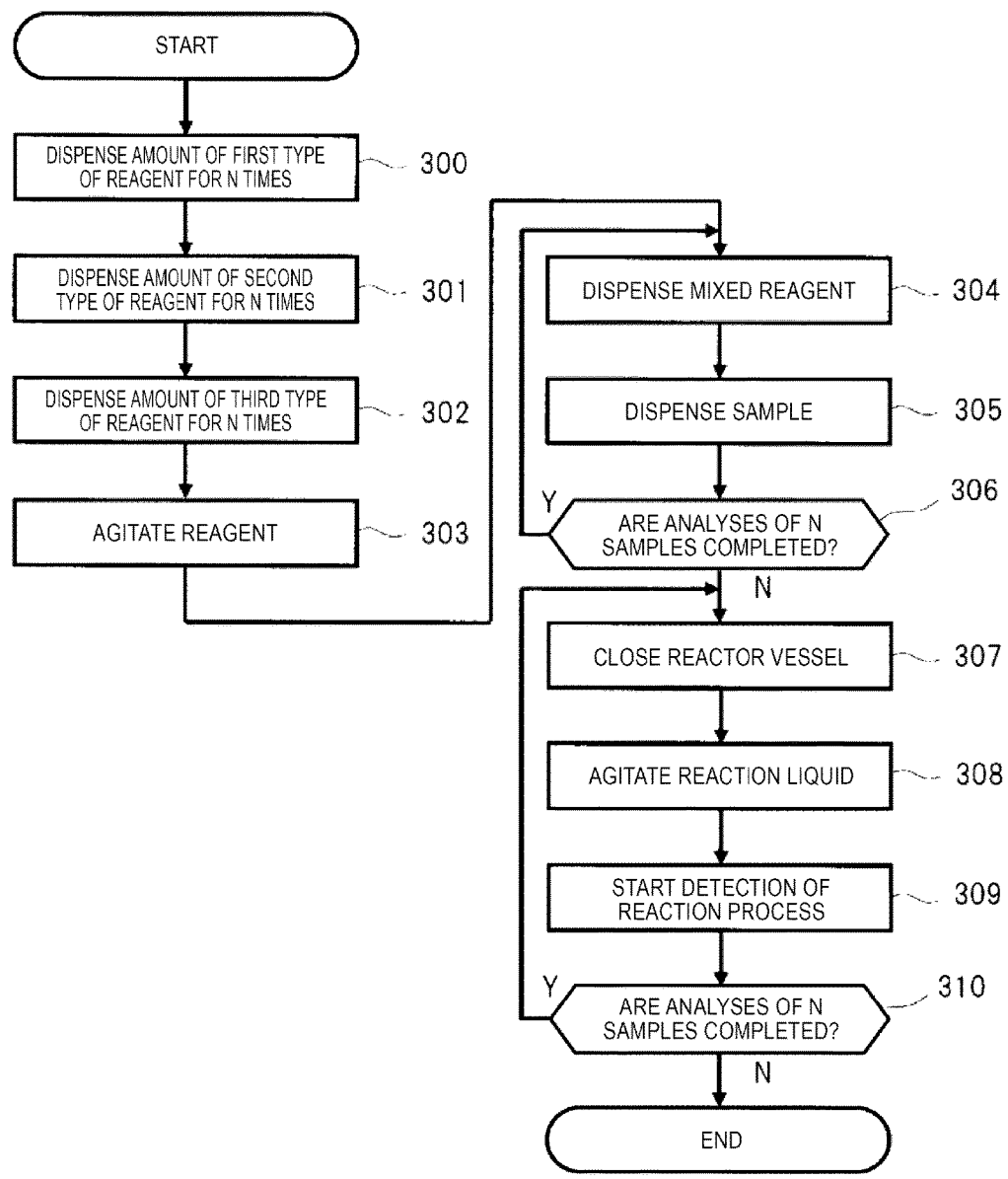

[Fig. 4]
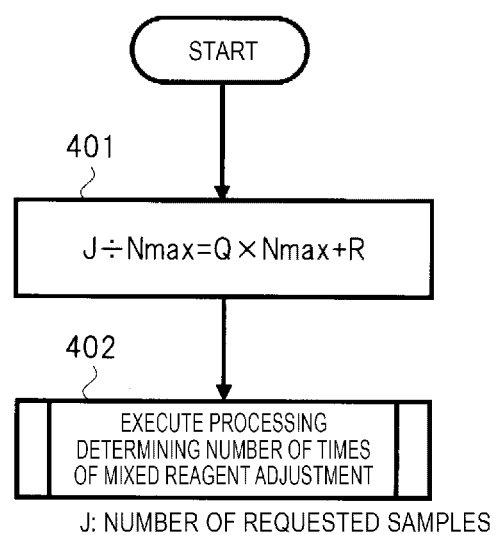

[Fig. 5]
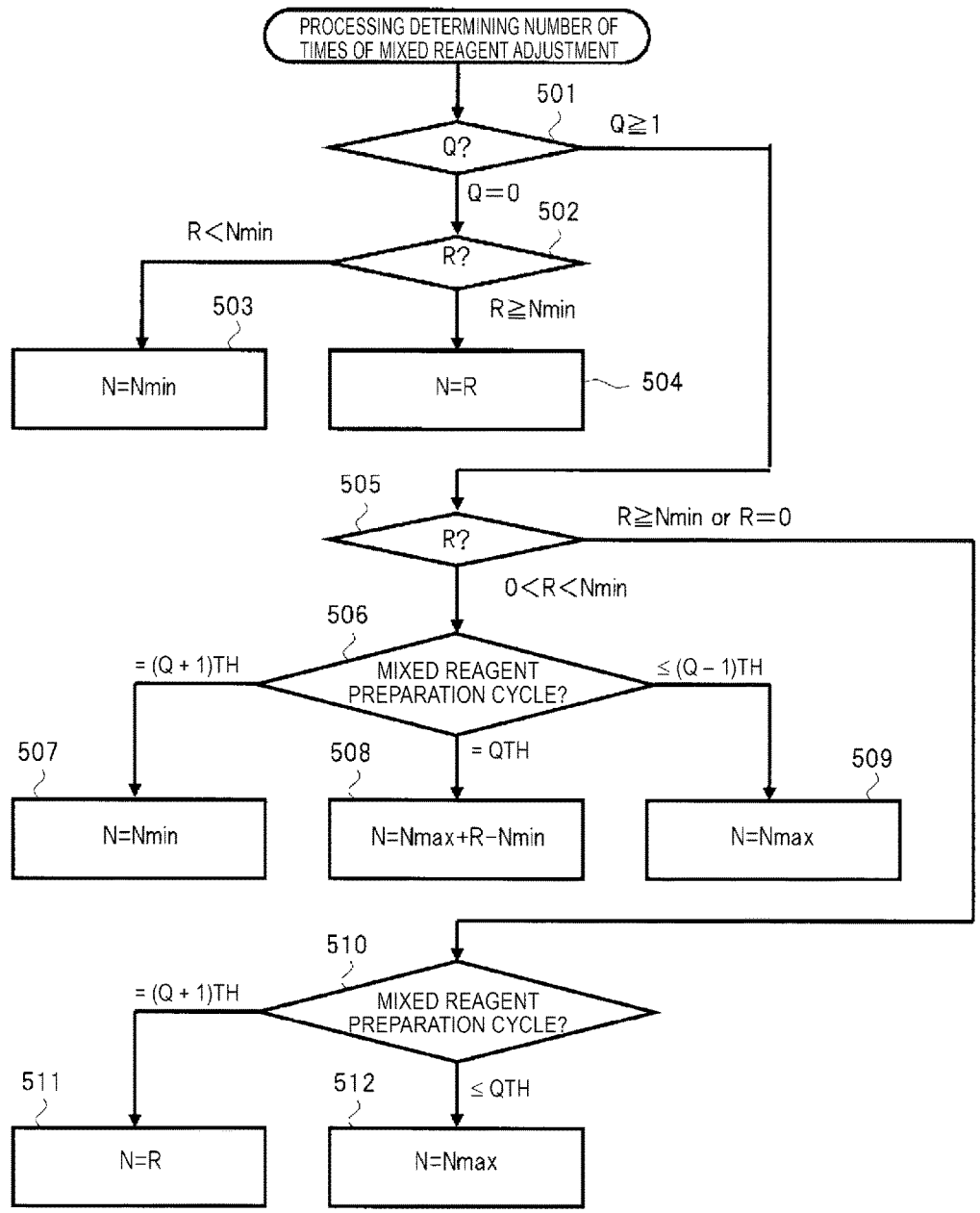

[Fig. 6]

| NUMBER OF REQUESTED SAMPLES | NUMBER OF TIMES OF MIXED REAGENT PREPARATION | NUMBER (N) OF TIMES OF MIXED REAGENT ADJUSTMENT | | |
|---|---|---|---|---|
| | | FIRST TIME | SECOND TIME | THIRD TIME |
| 1 | 1 | 4 | – | – |
| 2 | 1 | 4 | – | – |
| 3 | 1 | 4 | – | – |
| 4 | 1 | 4 | – | – |
| 5 | 1 | 5 | – | – |
| 6 | 1 | 6 | – | – |
| 7 | 1 | 7 | – | – |
| 8 | 1 | 8 | – | – |
| 9 | 2 | 5 | 4 | – |
| 10 | 2 | 6 | 4 | – |
| 11 | 2 | 7 | 4 | – |
| 12 | 2 | 8 | 4 | – |
| 13 | 2 | 8 | 5 | –– |
| 14 | 2 | 8 | 6 | – |
| 15 | 2 | 8 | 7 | – |
| 16 | 2 | 8 | 8 | – |
| 17 | 3 | 8 | 5 | 4 |
| 18 | 3 | 8 | 6 | 4 |
| 19 | 3 | 8 | 7 | 4 |
| 20 | 3 | 8 | 8 | 4 |
| 21 | 3 | 8 | 8 | 5 |
| 22 | 3 | 8 | 8 | 6 |
| 23 | 3 | 8 | 8 | 7 |
| 24 | 3 | 8 | 8 | 8 |

Nmin=4, Nmax=8

[Fig. 7]

NUMBER OF REQUESTED SAMPLES FOR REAGENT
ITEM A INDICATES TWO SAMPLES.  UPON THIS
REQUEST, AMOUNT OF UNUSED MIXED REAGENT FOR
TWO TIMES IS GENERATED.
IN ORDER TO PREVENT GENERATION OF UNUSED
MIXED REAGENT, NUMBER OF REQUESTED SAMPLES
NEEDS TO BE CHANGED SO AS TO BE FOUR OR MORE
SAMPLES.
IS IT REALLY OK TO START ANALYSIS?

OK    Cancel

[Fig. 8]
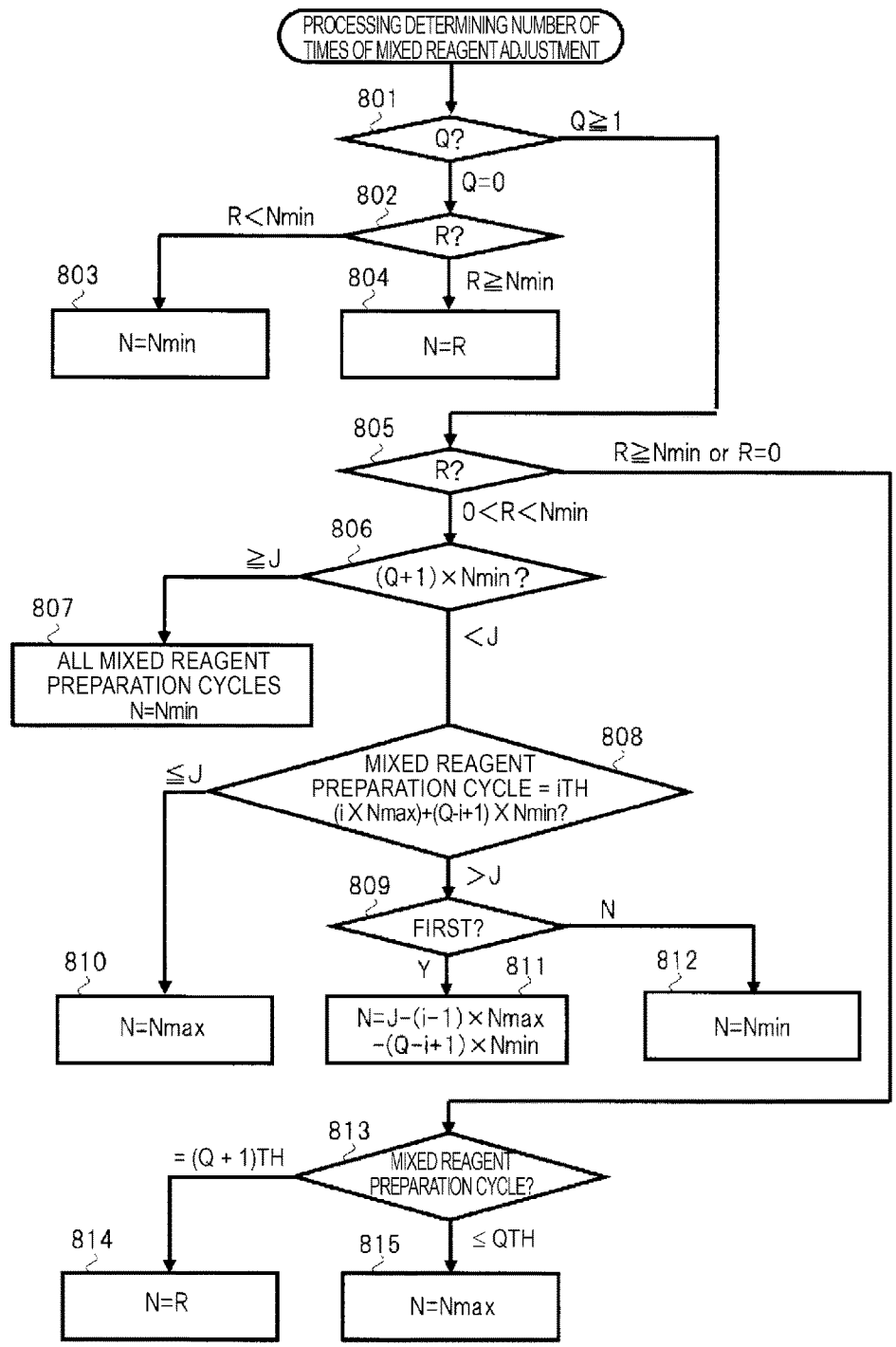

[Fig. 9]

| NUMBER OF REQUESTED SAMPLES | NUMBER OF TIMES OF MIXED REAGENT PREPARATION | NUMBER (N) OF TIMES OF MIXED REAGENT ADJUSTMENT | | | |
|---|---|---|---|---|---|
| | | FIRST TIME | SECOND TIME | THIRD TIME | FOURTH TIME |
| 1 | 1 | 5 | - | - | - |
| 2 | 1 | 5 | - | - | - |
| 3 | 1 | 5 | - | - | - |
| 4 | 1 | 5 | - | - | - |
| 5 | 1 | 5 | - | - | - |
| 6 | 1 | 6 | - | - | - |
| 7 | 1 | 7 | - | - | - |
| 8 | 2 | 5 | 5 | - | - |
| 9 | 2 | 5 | 5 | - | - |
| 10 | 2 | 5 | 5 | - | - |
| 11 | 2 | 6 | 5 | - | - |
| 12 | 2 | 7 | 5 | - | - |
| 13 | 2 | 7 | 6 | - | - |
| 14 | 2 | 7 | 7 | - | - |
| 15 | 3 | 5 | 5 | 5 | - |
| 16 | 3 | 6 | 5 | 5 | - |
| 17 | 3 | 7 | 5 | 5 | - |
| 18 | 3 | 7 | 6 | 5 | - |
| 19 | 3 | 7 | 7 | 5 | - |
| 20 | 3 | 7 | 7 | 6 | - |
| 21 | 3 | 7 | 7 | 7 | - |
| 22 | 4 | 7 | 5 | 5 | 5 |
| 23 | 4 | 7 | 6 | 5 | 5 |
| 24 | 4 | 7 | 7 | 5 | 5 |

Nmin=5, Nmax=7

[Fig. 10]
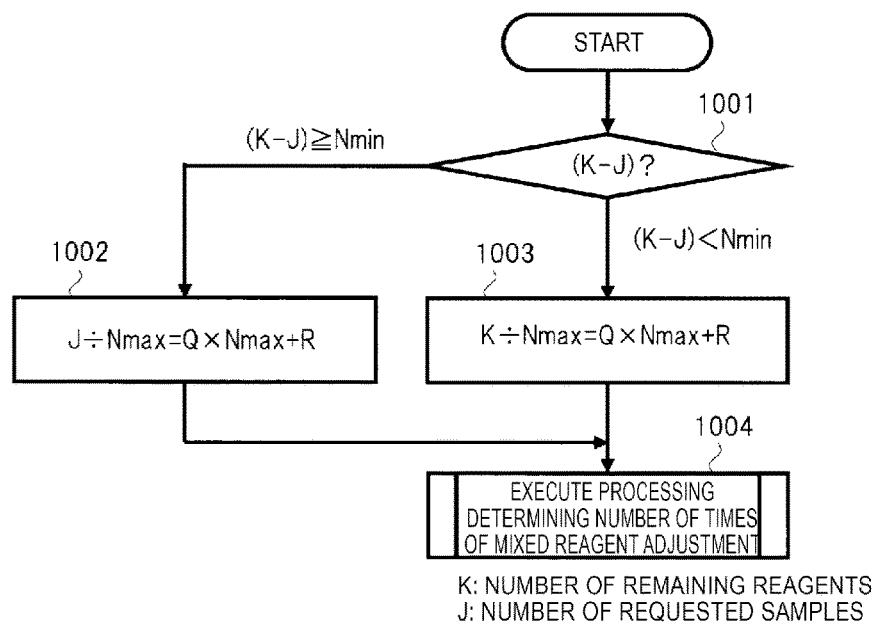

[Fig. 11]

| NUMBER OF REQUESTED SAMPLES | NUMBER OF TIMES OF MIXED REAGENT ADJUSTMENT (TOTAL) | NUMBER OF TIMES OF MIXED REAGENT PREPARATION | NUMBER OF TIMES OF MIXED REAGENT ADJUSTMENT | | NUMBER OF REMAINING REAGENTS AFTER MIXED REAGENT PREPARATION | NUMBER OF UNUSED MIXED REAGENTS |
|---|---|---|---|---|---|---|
| | | | FIRST TIME | SECOND TIME | | |
| 1 | 4 | 1 | 4 | – | 4 | 3 |
| 2 | 4 | 1 | 4 | – | 4 | 2 |
| 3 | 4 | 1 | 4 | – | 4 | 1 |
| 4 | 4 | 1 | 4 | – | 4 | 0 |
| 5 | 8 | 1 | 8 | – | 0 | 3 |
| 6 | 8 | 1 | 8 | – | 0 | 2 |
| 7 | 8 | 1 | 8 | – | 0 | 1 |
| 8 | 8 | 1 | 8 | – | 0 | 0 |

NUMBER (K) OF REMAINING REAGENTS=8, Nmin=4, Nmax=8

[Fig. 12]

| NUMBER OF REQUESTED SAMPLES | NUMBER OF TIMES OF MIXED REAGENT ADJUSTMENT (TOTAL) | NUMBER OF TIMES OF MIXED REAGENT PREPARATION | NUMBER OF TIMES OF MIXED REAGENT ADJUSTMENT | | NUMBER OF REMAINING REAGENTS AFTER MIXED REAGENT PREPARATION | NUMBER OF UNUSED MIXED REAGENTS |
|---|---|---|---|---|---|---|
| | | | FIRST TIME | SECOND TIME | | |
| 1 | 4 | 1 | 4 | – | 6 | 3 |
| 2 | 4 | 1 | 4 | – | 6 | 2 |
| 3 | 4 | 1 | 4 | – | 6 | 1 |
| 4 | 4 | 1 | 4 | – | 6 | 0 |
| 5 | 5 | 1 | 5 | – | 5 | 0 |
| 6 | 6 | 1 | 6 | – | 4 | 0 |
| 7 | 10 | 2 | 6 | 4 | 0 | 3 |
| 8 | 10 | 2 | 6 | 4 | 0 | 2 |
| 9 | 10 | 2 | 6 | 4 | 0 | 1 |
| 10 | 10 | 2 | 6 | 4 | 0 | 0 |

NUMBER (K) OF REMAINING REAGENTS=10, Nmin=4, Nmax=8

[Fig. 13A]

| NUMBER OF REQUESTED SAMPLES | NUMBER OF TIMES OF MIXED REAGENT ADJUSTMENT (TOTAL) | NUMBER OF TIMES OF MIXED REAGENT PREPARATION | NUMBER OF TIMES OF MIXED REAGENT ADJUSTMENT | | NUMBER OF REMAINING REAGENTS AFTER MIXED REAGENT PREPARATION | NUMBER OF UNUSED MIXED REAGENTS |
|---|---|---|---|---|---|---|
| | | | FIRST TIME | SECOND TIME | | |
| 1 | 4 | 1 | 4 | - | 4 | 3 |
| 2 | 4 | 1 | 4 | - | 4 | 2 |
| 3 | 4 | 1 | 4 | - | 4 | 1 |
| 4 | 4 | 1 | 4 | - | 4 | 0 |
| 5 | 5 | 1 | 5 | - | 3 | 0 |
| 6 | 6 | 1 | 6 | - | 2 | 0 |
| 7 | 7 | 1 | 7 | - | 1 | 0 |
| 8 | 8 | 1 | 8 | - | 0 | 0 |

NUMBER (K) OF REMAINING REAGENTS=8, Nmin=4, Nmax=8

[Fig. 13B]

| NUMBER OF REQUESTED SAMPLES | NUMBER OF TIMES OF MIXED REAGENT ADJUSTMENT (TOTAL) | NUMBER OF TIMES OF MIXED REAGENT PREPARATION | NUMBER OF TIMES OF MIXED REAGENT ADJUSTMENT | | NUMBER OF REMAINING REAGENTS AFTER MIXED REAGENT PREPARATION | NUMBER OF UNUSED MIXED REAGENTS |
|---|---|---|---|---|---|---|
| | | | FIRST TIME | SECOND TIME | | |
| 1 | 4 | 1 | 4 | - | 6 | 3 |
| 2 | 4 | 1 | 4 | - | 6 | 2 |
| 3 | 4 | 1 | 4 | - | 6 | 1 |
| 4 | 4 | 1 | 4 | - | 6 | 0 |
| 5 | 5 | 1 | 5 | - | 5 | 0 |
| 6 | 6 | 1 | 6 | - | 4 | 0 |
| 7 | 7 | 2 | 7 | - | 3 | 0 |
| 8 | 8 | 2 | 8 | - | 2 | 0 |
| 9 | 9 | 2 | 5 | 4 | 1 | 0 |
| 10 | 10 | 2 | 6 | 4 | 0 | 0 |

NUMBER (K) OF REMAINING REAGENTS=10, Nmin=4, Nmax=8

[Fig. 14]
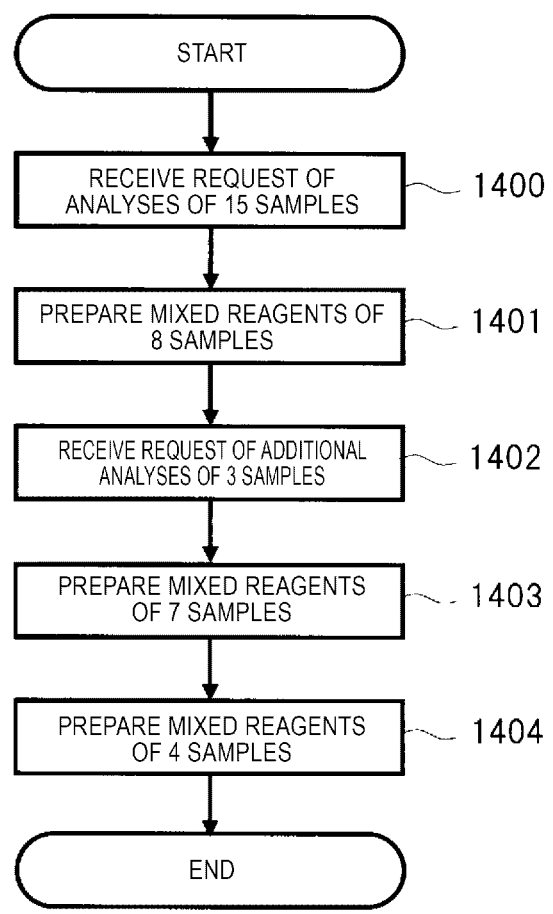

[Fig. 15]
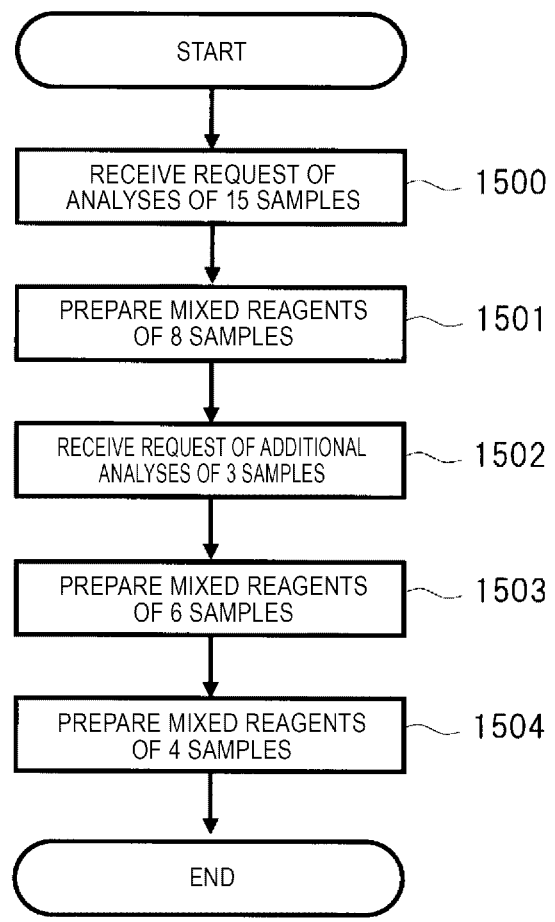

AUTOMATIC ANALYSIS DEVICE

TECHNICAL FIELD

The present invention relates to an automatic analysis device, and for example, relates to an automatic analysis device which performs a genetic test.

BACKGROUND ART

For example, there are known automatic analysis devices which automatically analyze organic reagents and are represented by a genetic testing device. When analyzing a desired composition (analysis item) of a requested sample by using the device, a reaction liquid adjustment step in which the reagents and the samples are dispensed by a liquid amount in accordance with an analysis protocol is performed, and then, a reaction process detection step in which a reaction process or a reaction result is monitored based on a predetermined reaction condition and a predetermined detection method is performed. In this case, in the reaction liquid adjustment step, the reagent to be dispensed is not limited to one type, and there is a case where several types of reagents such as a buffer solution, a primer, a fluorescence reagent, and the like are required to be dispensed.

In addition, a dispensing amount of the reagent and the sample is generally defined for each analysis item. However, a liquid amount thereof is variable, and if predetermined dispensing accuracy is not satisfied, accurate reaction speed and reaction efficiency cannot be maintained, thereby resulting in a bad influence in a reaction result. In order to satisfy the various types of dispensing accuracy, there is a case where the automatic analysis device has a mechanism in which dispensers having different capacities are included, dispensing chips having different capacities (for example, a 200-microliter chip and a 25-microliter chip) and the like are prepared, or the dispensing chips are mounted in the dispensers in accordance with the dispensing amount.

SUMMARY OF INVENTION

Technical Problem

For example, a primer and the like used in a genetic test are required to be dispensed in a minute amount such as 0.5 microliters for one analysis. In this manner, in a case of a reagent of which a reagent dispensing amount per analysis is small, it may be difficult to ensure desired dispensing accuracy. For example, in order to ensure desired dispensing accuracy, it is possible to consider preparation of dispensers and dispensing chips which are suitable for dispensing a minute amount. However, in this case, an increase in cost or size of a device is caused. Furthermore, in this case, processing in which several types of reagents are dispensed for each analysis is necessary. Therefore, the number of times of dispensing increases, and deterioration of throughput of the device is also caused. In addition, in order to ensure desired dispensing accuracy, it is possible to consider increasing an amount of the reagent which is used in one analysis (for example, 2 microliters are used in one analysis). However, in this case, the increased amount leads to an increase of reagent costs per analysis.

Therefore, as a method for solving the problem in dispensing a minute amount and reducing the influence to the throughput, in a case where several types of reagents (a buffer solution, a primer, a fluorescence reagent, and the like) are used in one analysis, it is useful to adopt a method in which solutions obtained by mixing several types of reagents used in one analysis are collectively prepared in advance in an amount of as many are necessary for multiple analyses. In this specification, the solution obtained by mixing several types of reagents is referred to as a mixed reagent. In a case of applying the mixed reagent, in a reaction liquid adjustment step, amounts of the mixed reagent and a sample required for one analysis may be dispensed from an amount of mixed reagent for multiple analyses prepared in advance.

If such a method is applied, when an amount of mixed reagent for multiple analyses is prepared, reagents in minute amounts in an amount of as many are necessary for multiple analyses are collectively dispensed. For example, even in a case of 0.5 microliters for one analysis, if an amount for 8 analyses is collectively dispensed, the amount becomes 4 microliters. Therefore, it is possible to satisfy the lower limit (for example, 2 microliters) of a dispensing accuracy guarantee range of the dispenser or the dispensing chip. In addition, when an amount required for one analysis is dispensed from the mixed reagent in the reaction liquid adjustment step, the required amount can generally satisfy the lower limit of the dispensing accuracy guarantee range as well, as a result of adding several types of reagents thereto.

Here, for example, in a case where an amount of mixed reagent for N analyses is prepared, the minimum value of N is set based on the lower limit of the dispensing accuracy guarantee range of the dispenser or the dispensing chip. Meanwhile, the maximum value of N is set based on the upper limit of the dispensing accuracy guarantee range of the dispenser or the dispensing chip, or the capacity of a vessel which is used when preparing the mixed reagent. In this specification, the value of N is referred to as the number of times of mixed reagent adjustment, and the minimum value and the maximum value of N are respectively referred to as the minimum number of times of mixed reagent adjustment and the maximum number of times of mixed reagent adjustment. The number of times of mixed reagent adjustment is a value equal to or greater than the minimum number of times of mixed reagent adjustment and equal to or less than the maximum number of times of mixed reagent adjustment.

For example, in a case of preparing a mixed reagent by using a reagent of 0.5 microliters for one analysis and a dispensing chip of which the lower limit of the dispensing accuracy guarantee range is 2 microliters, the minimum number of times of mixed reagent adjustment, that is, the minimum value of the number N of times of mixed reagent adjustment indicates the amount for 4 times. In addition, for example, in a case of preparing a mixed reagent by using a reagent of 25 microliters for one analysis and a dispensing chip of which the upper limit of the dispensing accuracy guarantee range is 200 microliters, the maximum number of times of mixed reagent adjustment, that is, the maximum value of the number N of times of mixed reagent adjustment indicates the amount for 8 times.

As described above, as the mixed reagent is prepared based on the number of times of mixed reagent adjustment, with respect to the reagent which is required to be dispensed in a minute amount and is thereby difficult to satisfy the dispensing accuracy with one analysis, it is possible to perform the analyses in a state where the dispensing accuracy is satisfied. However, for example, in a case where the number of times of mixed reagent adjustment is set to a fixed value at all times, depending on the number of requested samples (in other words, the required number of times of analysis), there is a case where a surplus of the mixed reagent is generated. In this specification, the surplus of the mixed reagent is referred to as an unused mixed reagent, and the number of times of analysis which can be executed with the unused mixed reagent is referred to as the number of unused mixed reagents. Generally, the mixed reagent has to be used within a predetermined period of time after the preparation, and an unused mixed reagent which has exceeded the predetermined period of time is subjected to being discarded. Therefore, a reduction of the unused mixed reagent subjected to being discarded and a reduction of reagent costs are demanded.

The present invention has been made in consideration of the above-described circumstances. An object thereof is to provide an automatic analysis device in which reagent costs can be reduced.

The above-described object, other objects, and new features of the present invention will be clarified according to the description of this specification and the accompanying drawings.

Solution to Problem

The overview of a representative embodiment in the invention disclosed in this application can be simply described as follows.

According to an automatic analysis device of the present embodiment, the device analyzes a sample by applying a mixed reagent in which a plurality of reagents are mixed together, and the device includes a mixed reagent preparation unit, a control unit, and a reaction liquid preparation unit. The mixed reagent preparation unit collectively prepares an amount of the mixed reagent s many as the number of times of analysis. The control unit sets the mixed reagent to be collectively prepared to a value within a range of a maximum value and a minimum value so as to minimize a surplus of the mixed reagent in a case where the maximum value and the minimum value are set to the mixed reagent to be collectively prepared and the number of times of analysis beyond the range of the maximum value and the minimum value of the mixed reagent to be collectively prepared are requested.

Advantageous Effects of Invention

According to the simply described effect which can be obtained through the representative embodiment in the invention disclosed in this application, it is possible to realize a reduction of reagent costs in an automatic analysis device.

BRIEF DESCRIPTION OF DRAWINGS

FIG. 1 is a schematic view illustrating a configuration example of an automatic analysis device of Embodiment 1 of the present invention.

FIG. 2 is a flow chart illustrating a schematic operational example of the automatic analysis device which is examined as the premise of the present invention.

FIG. 3 is a flow chart illustrating a schematic operational example of the automatic analysis device in FIG. 1.

FIG. 4 is a flow chart illustrating an example of processing contents applied when determining the number of times of mixed reagent adjustment in the automatic analysis device of Embodiment 1 of the present invention.

FIG. 5 is a flow chart illustrating an example of the detailed processing contents of the processing determining the number of times of mixed reagent adjustment in FIG. 4.

FIG. 6 is an explanatory diagram illustrating a specific example of the numbers of times of mixed reagent adjustment determined in accordance with the number of requested samples, in the flow of FIG. 4.

FIG. 7 is an explanatory diagram illustrating an example of an additional function which is useful while being entailed with the flow of FIG. 4.

FIG. 8 is a flow chart illustrating an example of the processing contents applied when determining the number of times of mixed reagent adjustment by using an alternative calculation formula in the automatic analysis device of Embodiment 1 of the present invention.

FIG. 9 is an explanatory diagram illustrating a specific example of the numbers of times of mixed reagent adjustment determined in accordance with the number of requested samples, in the flow of FIG. 8.

FIG. 10 is a flow chart illustrating an example of the processing contents applied when determining the number of times of mixed reagent adjustment in the automatic analysis device of Embodiment 2 of the present invention.

FIG. 11 is an explanatory diagram illustrating a specific example of the numbers of times of mixed reagent adjustment determined in accordance with the number of requested samples, the numbers of unused mixed reagents, and the numbers of remaining reagents, in the flow of FIG. 10.

FIG. 12 is an explanatory diagram illustrating another specific example of the numbers of times of mixed reagent adjustment determined in accordance with the number of requested samples, the numbers of unused mixed reagents, and the numbers of remaining reagents, in the flow of FIG. 10.

FIGS. 13A and 13B are explanatory diagrams respectively illustrating specific examples of the numbers of times of mixed reagent adjustment determined in accordance with the number of requested samples, the numbers of unused mixed reagents, and the numbers of remaining reagents which are sources of the unused mixed reagent, in the flow of FIG. 4.

FIG. 14 is a flow chart at the time of determining the number of times of mixed reagent adjustment in a case where the flow of FIG. 5 is executed without using Embodiment 4 of the present invention.

FIG. 15 is a flow chart at the time of determining the number of times of mixed reagent adjustment in the automatic analysis device according to Embodiment 4 of the present invention.

DESCRIPTION OF EMBODIMENTS

In embodiments described below, when there is a need for convenience, description will be divided into multiple sections or multiple embodiments. However, excluding a case of being particularly and specifically stated, those are not irrelevant to each other. One section or one embodiment has a relationship with respect to a different section or a different embodiment so as to be a modification example, details, a supplementary explanation, and the like thereof. In addition, in the embodiments described below, in a case where the number of elements, and the like (including number, numerical value, amount, range, and the like) is mentioned, excluding a case of being particularly and specifically stated, a case of being clearly limited to a particular number in principle, and the like, the number is not limited to the particular number. The number may be equal to, greater than, or smaller than the particular number.

Furthermore, in the embodiments described below, it is not necessary to mention that configuration elements thereof (including element Steps and the like) are not necessarily required, excluding a case of being particularly and specifically stated, a case of being considered to be required obviously in principle, and the like. Similarly, in the embodiments described below, when a shape, a positional relationship, and the like of the configuration elements and the like are mentioned, excluding a case of being particularly and specifically stated, a case of being considered not to be so obvious in principle, and the like, the shape, the positional relationship, and the like are assumed to substantially include that close to or similar to the shape and the like. The same can also be applied to the numerical value and the range mentioned above.

Hereinafter, embodiments of the present invention will be described in detail with reference to the drawings. In all the drawings for describing the embodiments, the same reference numerals and signs are generally applied to the same members, and repetitive description thereof will be omitted.

Embodiment 1

Schematic Configuration of Automatic Analysis Device

FIG. 1 is a schematic view illustrating a configuration example of an automatic analysis device of Embodiment 1 of the present invention. For example, the automatic analysis device illustrated in FIG. 1 is a genetic testing device 10 and is a device that analyzes a sample by applying a mixed reagent which is obtained by mixing a plurality of reagents together. The genetic testing device 10 includes a test unit 100, an input unit 123, a display unit 124, and a control unit 125. The test unit 100 includes a sample vessel rack 102, a reagent vessel rack 104, a mixed reagent adjustment vessel rack 106, a reactor vessel rack 108, a reaction liquid adjustment position 109, a closing unit 110, and an agitation unit 111.

The sample vessel rack 102 stores a plurality of sample vessels 101. Each of the sample vessels 101 contains a sample including a nucleic acid which is subjected to amplification processing. The reagent vessel rack 104 stores a plurality of reagent vessels 103. Each of the reagent vessels 103 contains various types of reagents which are added to the sample. The mixed reagent adjustment vessel rack 106 stores a plurality of mixed reagent adjustment vessels 105 for mixing reagents. The reactor vessel rack 108 stores a plurality of unused reactor vessels 107. Each of the reactor vessels 107 is a vessel for mixing the sample and the reagent.

At the reaction liquid adjustment position 109, the unused reactor vessels 107 are installed, and the sample and the mixed reagent are respectively dispensed from the sample vessels 101 and the mixed reagent adjustment vessels 105 to the reactor vessels 107. In the closing unit 110, processing of sealing the reactor vessels 107 containing reaction liquids each of which is a mixed liquid of a sample and a mixed reagent is performed by using a lid member (not illustrated). In the agitation unit 111, processing of agitating the reaction liquids which are contained in the sealed reactor vessels 107 is performed.

The test unit 100 also includes a robot arm device 118, a gripper unit 119, a dispensing unit 120, dispensing chip racks 113 and 115, a nucleic acid amplification unit 121, and a discard box 122. The robot arm device 118 includes a robot arm. X-shaft 116 which is disposed so as to extend in an X-axis direction (lateral direction in FIG. 1) on the test unit 100, and a robot arm Y-shaft 117 which is disposed so as to extend in a Y-axis direction (vertical direction in FIG. 1). The robot arm Y-shaft 117 is movable on the robot arm X-shaft 116. The gripper unit 119 is provided so as to be movable on the robot arm Y-shaft 117. The gripper unit 119 grips the reactor vessels 107 and transports the reactor vessels 107 to each section inside the test unit 100 while entailing movement of the above-described robot arm Y-shaft 117 itself.

The dispensing unit 120 is provided so as to be movable on the robot arm Y-shaft 117 and performs various types of dispensing processing while entailing movement of the above-described robot arm Y-shaft 117 itself. Specifically, the dispensing unit 120 performs the dispensing processing of preparing mixed reagents by suctioning each of the reagents in the reagent vessels 103 and discharging the reagents into the mixed reagent adjustment vessels 105. In this case, mainly, the reagent vessel rack 104, the mixed reagent adjustment vessel rack 106, and the dispensing unit 120 function as mixed reagent preparation units for preparing the mixed reagents.

In addition, the dispensing unit 120 suctions the sample in the sample vessel 101 and the mixed reagent in the mixed reagent adjustment vessel 105, thereby performing the dispensing processing of discharging the sample and the mixed reagent into the reactor vessels 107 placed at the reaction liquid adjustment position 109. In this case, the sample vessel rack 102, the mixed reagent adjustment vessel rack 106, the reaction liquid adjustment position 109, and the dispensing unit 120 function as reaction liquid preparation units for dispensing an amount of sample and mixed reagent for one analysis into each of the reactor vessels 107.

The dispensing chip racks 113 and 115 respectively store a plurality of unused dispensing chips 112 and 114. Without being particularly limited, the dispensing chips 112 have large capacity (for example, 200 microliters), and the dispensing chips 114 have small capacity (for example, 25 microliters). Each of the dispensing chips 112 and 114 is mounted at a nozzle tip end portion and is brought into contact with a sample or a reagent inside the dispensing unit 120 when the dispensing unit 120 performs the dispensing processing.

In the nucleic acid amplification unit 121, nucleic acid amplification processing, and fluorescence detection (reaction process detection) of the amplification process are performed with respect to the reaction liquids which are contained in the reactor vessels 107. In the discard box 122, used dispensing chips 112 and 114 or used (tested) reactor vessels 107 are discarded. The input unit 123 is configured to include a keyboard, a mouse, and the like. The display unit 124 is configured to include a liquid crystal monitor and the like. The control unit 125 controls the overall operation of the test unit 100.

Each of the sample vessels 101 is managed for each contained sample based on identification information such as bar codes and the like, and is managed based on positional information such as coordinates and the like allocated to each position of the sample vessel rack 102. Similarly, each of the reagent vessels 103 is managed for each contained reagent based on the identification information such as bar codes and the like, and is managed based on the positional information such as the coordinates and the like allocated to each position of the reagent vessel rack 104. The identification information and the positional information are registered in the control unit 125 in advance and are thereby managed. In addition, each of the mixed reagent adjustment vessels 105 and the reactor vessels 107 is similarly managed based on the identification information and the positional information.

The control unit 125 includes at least an analysis plan section 125a, an analysis execution section 125b, and a data processing section 125c. The analysis plan section 125a sets an analytic operation plan (scheduling) in accordance with a predetermined analytic condition which is designated through the input unit 123 and the display unit 124. The analysis execution section 125b controls each mechanism inside the test unit 100 in accordance with the analytic operation plan. The data processing section 125c manages fluorescence detection data and the like for each reactor vessel 107. For example, the input unit 123, the display unit 124, and the control unit 125 are configured to be a computer system such as a personal computer (PC) or the like.

Schematic Operation of Automatic Analysis Device (Comparison Example)

FIG. 2 is a flow chart illustrating a schematic operational example of the automatic analysis device which is examined as the premise of the present invention. In the genetic testing device, in a case where an amount of mixed reagent for a plurality of analyses is not prepared in advance, for example, processing illustrated in FIG. 2 is performed. Here, description will be given regarding a case where analyses for N samples are requested while an amount for one analysis is considered to be one requested sample and a case where three types of reagents are required in the genetic test. In the flow of FIG. 2, first, the three types of reagents are sequentially dispensed into the reactor vessels through Steps 200 to 202, agitation of reagents is performed in Step 203, and the mixed reagent is thereby prepared inside the reactor vessel.

Subsequently, in Step 204, one sample is dispensed into the reactor vessel, and the reaction liquid is prepared. There is a case where processing of dispensing evaporation preventing mineral oil or the like is added after Step 204 (not illustrated). Thereafter, the reactor vessel is sealed by the lid member in Step 205, a reaction liquid agitation operation is performed in Step 206, and detection of the reaction process starts in Step 207. Then, in Step 208, the steps through Steps 200 to 207 are repeated N times, thereby completing the analyses of N requested samples.

In a case where such a flow is applied, as described above, in a case of a reagent of which the reagent dispensing amount per analysis is small (for example, the reagent dispensing amount of a primer used in the genetic test is 0.5 microliters per analysis), the reagent dispensing amount becomes equal to or less than the lower limit of the dispensing accuracy (for example, 2 microliters) of the device, and thus, it is difficult to satisfy the dispensing accuracy. Therefore, as illustrated in FIG. 3, it is useful to adopt a method of satisfying the dispensing accuracy by collectively preparing an amount of mixed reagent for a plurality of analyses.

Schematic Operation of Automatic Analysis Device (Present Embodiment)

FIG. 3 is a flow chart illustrating a schematic operational example of the automatic analysis device in FIG. 1. In this case as well, description will be given regarding a case where N requested samples are analyzed and a case where three types of reagents are required in the genetic test. First, through Steps 300 to 303 in FIG. 3, a mixed reagent preparation cycle is executed. Specifically, through Steps 300 to 302 in FIG. 3, the mixed reagent preparation unit including the above-described dispensing unit 120 collectively dispenses the amount of three types of reagents for N analyses contained in each of the plurality of reagent vessels 103 into the mixed reagent adjustment vessels 105 so as to be dispensed as many as the number of times of mixed reagent adjustment. Subsequently, in Step 303, the mixed reagent preparation unit performs agitation of reagent and prepares the mixed reagent inside the mixed reagent adjustment vessels 105 based on the number of times of mixed reagent adjustment=N.

Subsequently, in Step 304, the reaction liquid preparation unit including the above-described dispensing unit 120 dispenses the amount of mixed reagent for one analysis from the amount of the mixed reagent for N analyses inside the mixed reagent adjustment vessels 105 into the reactor vessel 107 placed at the reaction liquid adjustment position 109. Furthermore, in Step 305, the reaction liquid preparation unit dispenses one sample inside the sample vessel 101 into the reactor vessel 107. Accordingly, the reaction liquid preparation unit prepares the reaction liquid inside the reactor vessel 107. There is a case where the processing of dispensing evaporation preventing mineral oil or the like is added after Step 305 (not illustrated). Then, in Step 306, the genetic testing device 10 repeats the steps of Steps 304 and 305 N times, thereby preparing N reaction liquids inside N reactor vessels 107.

Thereafter, in Step 307, the closing unit 110 seals the N reactor vessels 107 including the reaction liquids by using the lid member. In Step 308, the agitation unit 111 performs the agitation operation of the reaction liquids. In Step 309, the nucleic acid amplification unit 121 starts detection of the reaction process. Then, in Step 310, the genetic testing device 10 repeats the steps N times through Steps 307 to 309, thereby completing the analysis of the N requested samples.

By applying the flow of FIG. 3, for example, even in a case where there is a reagent of 0.5 microliters per analysis, if the number (N) of times of mixed reagent adjustment is 8, the reagent of 4 microliters is dispensed by collectively dispensing an amount for eight analyses, and thus, the reagent dispensing amount is within the dispensing accuracy range of the device. Generally, a reagent such as a primer which requires minute amount dispensing and a reagent such as a buffer solution of which dispensing amount per analysis is within the dispensing accuracy range of the device are included inside the mixed reagent. Therefore, the dispensing accuracy does not become a problem when dispensing the mixed reagent in Step 304.

In addition, when the number of times of mixed reagent adjustment is N, and the number of reagents required in preparation of the mixed reagent is M, the number of times of dispensing becomes (MN+N) times in a case of FIG. 2 where an amount of mixed reagent for a plurality of analyses is not prepared, and the number of times of dispensing becomes (M+2N) times in a case of FIG. 3 where an amount of mixed reagent for a plurality of analyses is prepared. If the number of times of dispensing in a case of FIG. 3 is subtracted from the number of times of dispensing in a case of FIG. 2, the result becomes {N(M−1)−M}, and this value is equal to or greater than zero under the condition of N≥2 and M≥2. In other words, it is possible to reduce the number of times of dispensing by applying the flow of FIG. 3, compared to a case where the flow of FIG. 2 is applied, and thus, the throughput of the device can be improved.

As described above, by preparing an amount of mixed reagent for a plurality of analyses in advance, even in an analysis in which a reagent requiring minute amount dispensing is applied, it is possible to configure the automatic analysis device in which the dispensing accuracy is satisfied and the throughput of the device can be improved. However, as described above, in a case where the number (N) of times of mixed reagent adjustment is set to be a fixed value at all times, in accordance with the number of requested samples, there is a case where a surplus mixed reagent (unused mixed reagent) is generated. For example, a case where the maximum number of times of mixed reagent adjustment is set to 8, and the number (N) of times of mixed reagent adjustment is set to 8 at all times is assumed. Here, in a case where the number of requested samples is 9, 8 samples are processed at the first stage in the flow of FIG. 3, and the mixed reagent having the number of times of mixed reagent adjustment=8 with respect to one remaining sample is prepared at the second stage in the flow of FIG. 3. As a result thereof, it is possible to generate an amount of unused mixed reagent for seven analyses.

Processing of Determining Number of Times of Mixed Reagent Adjustment

In the present Embodiment 1, in accordance with the number of requested samples, the minimum number of times of mixed reagent adjustment, and the maximum number of times of mixed reagent adjustment, the number (N) of times of mixed reagent adjustment is variably determined so that the number of unused mixed reagents is minimized when the analysis is completed. FIG. 4 is a flow chart illustrating an example of the processing contents applied when determining the number of times of mixed reagent adjustment in the automatic analysis device of Embodiment 1 of the present invention. FIG. 5 is a flowchart illustrating an example of the detailed processing contents of the processing determining the number of times of mixed reagent adjustment in FIG. 4. The flows illustrated in FIGS. 4 and 5 are mainly executed by the analysis plan section 125a inside the control unit 125 of FIG. 1.

The processing determining the number of times of mixed reagent adjustment of the present embodiment is not necessarily executed by the analysis plan section 125a. For example, it is possible to determine the number of times of mixed reagent adjustment for each mixed reagent preparation cycle by retaining and using results of the processing determining the number of times of mixed reagent adjustment calculated in advance inside the control unit 125 in a form of matrix, for example. Otherwise, it is possible to adopt a form in which the number of times of mixed reagent adjustment for each mixed reagent preparation cycle set through the processing determining the number of times of mixed reagent adjustment from the outside of the control unit 125 is designated via the input unit 123, communication, or the like. In this manner, it is possible to reduce the number of times of calculation processing performed by the analysis plan section 125a and to accelerate the processing.

In FIG. 4, as indicated in Step 401, the analysis plan section 125a first calculates Expression (1) based on the number (J) of samples of which analyses are requested (the number of requested samples) and the maximum number (Nmax) of times of mixed reagent adjustment set in advance, thereby calculating an integral quotient Q and a remainder R. Here, one sample denotes an amount of sample for one analysis. Subsequently, as indicated in Step 402, the analysis plan section 125a executes the processing determining the number of times of mixed reagent adjustment illustrated in FIG. 5 by using the integral quotient Q and the remainder R based on Expression (1).

$$J/N\text{max} = Q \times N\text{max} + R \quad (1)$$

Here, the minimum number of times of executing the flow of FIG. 3 (that is, the mixed reagent preparation cycle) within the dispensing accuracy range becomes Q+1.

In FIG. 5, N is the number of times of mixed reagent adjustment, and Nmin is the minimum number of times of mixed reagent adjustment. As illustrated in FIG. 5, in a case of Q=0 in Step 501 and R<Nmin in Step 502, the analysis plan section 125a sets N=Nmin as indicated in Step 503. This case is a case of 1≤the number (J) of requested samples<Nmin. Even though an unused mixed reagent is generated by setting the number (N) of times of mixed reagent adjustment to the minimum number (Nmin) of times of mixed reagent adjustment, it is possible to minimize the number of unused mixed reagents.

In a case of Q=0 in Step 501 and R≥Nmin in Step 502, the analysis plan section 125a sets N=R as indicated in Step 504. This case is a case of Nmin≤the number (J) of requested samples<Nmax. It is possible to set the unused mixed reagent to zero by setting the number (N) of times of mixed reagent adjustment to the remainder R which is equal to the number (J) of requested samples.

In a case of Q≥1 in Step 501 and 0<R<Nmin in Step 505, the analysis plan section 125a variably sets N depending on how many times of the flow of FIG. 3 is executed (that is, how many cycles of the mixed reagent preparation cycle through Steps 300 to 303 are executed). Specifically, in a case of being equal to or less than (Q−1)th, N=Nmax as indicated in Step 509, in a case of Qth, N=Nmax+R−Nmin as indicated in Step 508, and in a case of (Q+1)th, N=Nmin as indicated in Step 507.

This case is a case where if the flow of FIG. 3 is executed by applying the maximum number of times of mixed reagent adjustment with respect to the samples more than the maximum number (Nmax) of times of mixed reagent adjustment, an unused mixed reagent ranging from 1 to less than the minimum number (Nmin) of times of mixed reagent adjustment is generated when the analyses of all the samples of which analyses are requested are completed. Therefore, in the process in which the flow of FIG. 3 (that is, the mixed reagent preparation cycle) is executed multiple times, in order to improve the throughput of the device, the samples are analyzed by applying the maximum number of times of mixed reagent adjustment as much as possible. As a result thereof, the samples as many as (the maximum number of times of mixed reagent adjustment+the remainder R) remaining at the final stage are processed in twice. In one process therebetween, the samples are analyzed by using the minimum number of times of mixed reagent adjustment. In the other process therebetween, the samples in the number of remaining (the maximum number of times of mixed reagent adjustment+the remainder R−the minimum number of times of mixed reagent adjustment) are analyzed by applying the number of times of mixed reagent adjustment as many as the number thereof.

Accordingly, the unused mixed reagent can be zero. It is possible to suitably change the number of times of execution in the flow of FIG. 3 to which Steps 507 to 509 are applied (that is, how many cycles of the mixed reagent preparation cycle). In other words, while the mixed reagent preparation cycle is executed (Q+1) times, without questioning the order, Step 507 and Step 508 may be respectively executed once in two cycles thereamong. In addition, in a case of Q≥2, Step 509 may be executed in the remaining cycles excluding the two cycles.

In a case of Q≥1 in Step 501 and R≥Nmin or R=0 in Step 505, the analysis plan section 125a variably sets N depending on how many times of the flow of FIG. 3 is executed (that is, how many cycles of the mixed reagent preparation cycle are executed). Specifically, in a case of being equal to or less than Qth, N=Nmax as indicated in Step 512, and in a case of (Q+1)th, N=R as indicated in Step 511.

This case is a case where if the flow of FIG. 3 is executed by applying the maximum number of times of mixed reagent adjustment with respect to the samples equal to or more than the maximum number (Nmax) of times of mixed reagent adjustment, an unused mixed reagents equal to or more than the minimum number (Nmin) of times of mixed reagent adjustment is generated or no unused mixed reagent is generated when the processing of all the samples is completed. Therefore, in the process in which the flow of FIG. 3 (that is, the mixed reagent preparation cycle) is executed multiple times, in order to improve the throughput of the device, the samples are processed by applying the maximum number of times of mixed reagent adjustment as much as possible, and the samples as many as the number of the remainders R which remain at the final stage are processed in one process by applying the number (N) of times of mixed reagent adjustment as many as the number thereof. Accordingly, the unused mixed reagent can be zero. In Steps 511 and 512, the order is not questioned similar to the case of Steps 507 to 509, while the mixed reagent preparation cycle is executed (Q+1) times, Step 511 may be executed in one cycle thereamong, and Step 512 may be executed in the remaining cycles excluding the one cycle.

FIG. 6 is an explanatory diagram illustrating a specific example of the number of times of mixed reagent adjustment determined in accordance with the number of requested samples, in the flow of FIG. 4. FIG. 6 illustrates a case where the maximum number (Nmax) of times of mixed reagent adjustment is set to 8 and the minimum number (Nmin) of times of mixed reagent adjustment is set to 4, and illustrates the number (N) of times of mixed reagent adjustment in a case where the number (J) of requested samples ranges from 1 to 24. As illustrated in FIG. 6, in a case where the number of requested samples is equal to or less than 4, the number of times of mixed reagent adjustment becomes 4 which is the minimum number of times of mixed reagent adjustment. In this case, 3, 2, and 1 of the unused mixed reagent is respectively generated in a case where the numbers of requested samples are 1, 2, and 3.

Meanwhile, in a case where the number of requested samples is equal to or greater than 4, no unused mixed reagent is generated as illustrated in FIG. 6. For example, in a case where the number of requested samples is 9 (Q=1, R=1), the flow of FIG. 3 is executed by applying the number of times of mixed reagent adjustment=5 via Step 508 in FIG. 5. Thereafter, the flow of FIG. 3 is executed by applying the number of times of mixed reagent adjustment=4 via Step 507 in FIG. 5. In addition, in a case where the number of requested samples is 13 (Q=1, R=5), the flow of FIG. 3 is executed by applying the number of times of mixed reagent adjustment=8 via Step 512 in FIG. 5. Thereafter, the flow of FIG. 3 is executed by applying the number of times of mixed reagent adjustment=5 via Step 511 in FIG. 5.

Additional Function Entailed by Processing Determining Number of Times of Mixed Reagent Adjustment FIG. 7 is an explanatory diagram illustrating an example of an additional function which is useful while being entailed with the flow of FIG. 4. As illustrated in FIG. 6, in a case where the number of requested samples is less than the minimum number (Nmin) of times of mixed reagent adjustment, an unused mixed reagent is generated. Specifically, this case corresponds to a case where Step 503 in FIG. 5 is executed. Therefore, as a more preferable form, in a case where an unused mixed reagent is generated, the control unit 125 causes a warning screen illustrated in FIG. 7, for example, to be displayed when receiving a request of analyzing a sample or starting an analysis, thereby notifying a user of a fact that the unused mixed reagent is generated. For example, the warning screen is displayed as the analysis plan section 125a inside the control unit 125 controls the display unit 124.

In FIG. 7, the item name of the reagent generating the unused mixed reagent, the number of requested samples thereof, and the number of requested samples for preventing generation of the unused mixed reagent are included in displaying. However, the displaying is not limited to displaying of all the aforementioned elements. In addition, in a state where the display unit 124 displays the number of requested samples for preventing generation of the unused mixed reagent in advance, a user may input a request of analysis.

Determination of Number of Times of Mixed Reagent Adjustment Performed Through Alternative Calculation Formula Here, the flow through Steps 505 to 509 in FIG. 5 is useful under the condition of Nmax≥2Nmin−1. In other words, in a case of Nmin+1≤Nmax≤2Nmin−2, there is a case of N<Nmin in Step 508. Therefore, in the automatic analysis device having the condition of Nmin+1≤Nmax≤2Nmin−2, the flow of FIG. 8 is executed. It is possible to apply the flow of FIG. 8 to a case of Nmax≥2Nmin−1.

In FIG. 8, Steps 801 to 805 are similar to Steps 501 to 505, and Steps 813 to 815 are similar to Steps 510 to 512. The difference between FIGS. 5 and 8 is setting of the number of times of the mixed reagent preparation performed through Steps 806 to 812, in a case of Q≥1 in Step 801 (501) and 0<R<Nmin in Step 805 (505).

In Step 806, in a case of (Q+1)×Nmin≥J, as indicated in Step 807, the analysis plan section 125a sets N=Nmin in all the mixed reagent adjustment cycles. In this case, the flow of FIG. 3 (that is, the mixed reagent preparation cycle) is executed Q+1 times so as to be within the dispensing accuracy range, and all the mixed reagent preparation cycles are executed by the minimum number (Nmin) of times of mixed reagent adjustment. In this case, even though an unused mixed reagent is generated, the number of unused mixed reagents can be minimized.

In this manner, in the automatic analysis device having the condition of Nmin+1≤Nmax≤2Nmin−2, in a case of J≥Nmin, via Step 807, there is a case where an unused mixed reagent is generated. However, in a case of Nmax≥2Nmin−1, in J≥Nmin, no unused mixed reagent is generated. Therefore, more preferably, the automatic analysis device may be configured so as to have the condition of Nmax≥2Nmin−1.

The analysis plan section 125a executes Step 808 in a case of (Q+1)×Nmin<J in Step 806. In Step 808, the analysis plan section 125a calculates (i×Nmax)+(Q−i+1)×Nmin in accordance with the number i of cycles of the mixed reagent preparation cycle. Then, in a case of (i×Nmax)+(Q−i+1)×Nmin≤J, the analysis plan section 125a sets N=Nmax as indicated in Step 810, thereby executing Step 809 in a case of (i×Nmax)+(Q−i+1)×Nmin>J. Here, in a case where Step 809 is executed for the first time, as indicated in Step 811, the analysis plan section 125a sets N=J−(i−1)×Nmax−(Q−i+1)×Nmin, and in a case where Step 809 is executed for the second time or after, as indicated in Step 812, the analysis plan section 125a sets N=Nmin.

In addition, by applying the flow of FIG. 8, the numbers of times of mixed reagent adjustment from 1 to (Q+1) times are calculated. However, it is possible to change the execution order within a range from 1 to (Q+1)th mixed reagent adjustment cycles.

FIG. 9 is an explanatory diagram illustrating a specific example of the numbers of times of mixed reagent adjustment determined in accordance with the number of requested samples, in the flow of FIG. 8. FIG. 9 illustrates a case where the maximum number (Nmax) of times of mixed reagent adjustment is set to 7, and the minimum number (Nmin) of times of mixed reagent adjustment is set to 5, and illustrates the number (N) of times of mixed reagent adjustment in a case where the number (J) of requested samples ranges from 1 to 24. As illustrated in FIG. 9, in a case where the number of requested samples is equal to or less than 5, the number of times of mixed reagent adjustment becomes 5 which is the minimum number of times of mixed reagent adjustment. In this case, 4, 3, 2, and 1 of the unused mixed reagent is respectively generated in a case where the numbers of requested samples are 1, 2, 3, and 4.

In a case where the number of requested samples is equal to or greater than 5 (Nmin), a surplus reagent is generated when the number of requested samples is 8 to 9 in the flow of FIG. 8. For example, in a case where the number of requested samples is 9 (Q=1, R=2), via Step 807 in FIG. 8, each of two mixed reagent adjustment cycles is executed under the condition of the number of times of mixed reagent adjustment=5. Meanwhile, in the flow of FIG. 5, in a case where the number of requested samples is 9 (Q=1, R=2), execution of Step 508 results in N=4. Accordingly, the number of times of mixed reagent adjustment less than the minimum number (Nmin) of times of mixed reagent adjustment is calculated, thereby being out of the dispensing accuracy range. In this manner, by applying the flow of FIG. 8, even though an unused reagent is generated, the mixed reagent preparation cycle can be executed within the dispensing accuracy range.

In addition, for example, in the flow of FIG. 5, in a case where the number of requested samples is 23 (Q=3, R=1), via Step 509, by applying the number of times of mixed reagent adjustment=7, the first and second flows of FIG. 3 are executed. In this case, an amount of mixed reagent for 14 times is prepared, and there is a need to prepare the mixed reagents as many as the amount of 9 remaining samples as the difference with respect to the 23 requested samples. In this case, execution of Step 508 results in N=4. Accordingly, the number of times of mixed reagent adjustment less than the minimum number (Nmin) of times of mixed reagent adjustment is calculated, thereby being out of the dispensing accuracy range. In addition, under such a condition, it is possible to set N=Nmin. However, in this case, with respect to the samples of the 9 remaining requested samples, the numbers of times of mixed reagent adjustment=5 for the third and fourth times, that is, an amount of mixed reagent for 10 times is prepared. Therefore, the number of remaining reagents=1 is generated.

Meanwhile, in the flow of FIG. 8, in a case where the number of requested samples is 23 (Q=3, R=1), via Step 810, by applying the number of times of mixed reagent adjustment=7, the first flow of FIG. 3 is executed. Thereafter, via Step 811, by applying the number of times of mixed reagent adjustment=6, the second flow of FIG. 3 is executed. Similarly, thereafter, via Step 811, by applying the number of times of mixed reagent adjustment=5, the third and fourth flows of FIG. 3 are executed, and thus, the unused mixed reagent can be zero.

Hereinbefore, by applying the automatic analysis device of the present Embodiment 1, based on the number of requested samples, the minimum number of times of mixed reagent adjustment, and the maximum number of times of mixed reagent adjustment, so as to minimize the number of unused mixed reagents, it is possible to determine the number of times of preparing the mixed reagent (the number of mixed reagent preparation cycles) and the number of times of mixed reagent adjustment for each cycle. As a result thereof, representatively, it is possible to reduce the unused mixed reagent which is subjected to being discarded and to reduce the reagent costs. In addition, by applying the mixed reagent, it is possible to ensure the dispensing accuracy and to improve the throughput of the device.

Embodiment 2

In the above-described Embodiment 1, in order to prevent generation of the unused mixed reagent, the number of times of mixed reagent adjustment for each mixed reagent preparation cycle is variably set. In the present Embodiment 2, in a different manner, in order to prevent a surplus of the reagent which is a source of the mixed reagent, depending on cases, it is characterized in that the number of times of mixed reagent adjustment is set so as to deliberately prepare the unused mixed reagent.

Problem as Premise of Present Embodiment 2

FIGS. 13(a) and 13(b) are explanatory diagrams respectively illustrating specific examples of the numbers of times of mixed reagent adjustment determined in accordance with the number of requested samples, the numbers of unused mixed reagents, and the numbers of remaining reagents which are sources of the unused mixed reagent, in the flow of FIG. 4. For example, a case where the number of remaining reagents is 1 denotes that an amount of reagent for one analysis remains. In FIG. 13 (a), similar to the case of FIG. 6, in a case where the maximum number (Nmax) of times of mixed reagent adjustment is set to 8, the minimum number (Nmin) of times of mixed reagent adjustment is set to 4, and the number of remaining reagents (the number (K) of remaining reagents) is set to 8, and in a case where the number of requested samples ranges from 1 to 8, the numbers of times of mixed reagent adjustment, the numbers of remaining reagents, and the numbers of unused mixed reagents are illustrated.

For example, in a case where the number of requested samples=1 to 3, similar to the case of FIG. 6, the processing is performed by applying the minimum number of times of mixed reagent adjustment. As a result, an unused mixed reagent is generated, four reagents are reduced, and the number of remaining reagents becomes 4. Since the number of remaining reagents=4 is equal to or greater than the minimum number of times of mixed reagent adjustment, it is possible to be used next time as the material of the mixed reagent. Meanwhile, in a case of the number of requested samples=5 to 7, similar to the case of FIG. 6, analyses are performed by respectively applying the number of times of mixed reagent adjustment=5 to 7. As a result, though the unused mixed reagent becomes zero, the number of remaining reagents=3 to 1 is generated. Since the number of remaining reagents=3 to 1 is less than the minimum number of times of mixed reagent adjustment, it is not possible to be used as the material of the mixed reagent thereafter.

In FIG. 13 (b), being different from the case of FIG. 13(a), in a case where the number (K) of remaining reagents is set to 10, and in a case where the number of requested samples ranges from 1 to 10, the numbers of times of mixed reagent adjustment, the numbers of remaining reagents, and the numbers of unused mixed reagents are illustrated. For example, in a case of the number of requested samples=7 and 8, similar to the case of FIG. 6, the processing is performed by respectively applying the number of times of mixed reagent adjustment=7 and 8. As a result, though the unused mixed reagent becomes zero, the number of remaining reagents=3 and 2 is respectively generated. In addition, in a case where the number of requested samples is set to 9, similar to the case of FIG. 6, the processing is performed by applying the number of times of mixed reagent adjustment=5 and the number of times of mixed reagent adjustment=4. As a result, though the unused mixed reagent becomes zero, the number of remaining reagents=1 is generated. Since the number of remaining reagents=3 to 1 is less than the minimum number of times of mixed reagent adjustment, it is not possible to be used as the material of the mixed reagent thereafter.

In this manner, in a case where there is a surplus of the reagent less than the minimum number (Nmin) of times of mixed reagent adjustment, the mixed reagent cannot be prepared by applying the reagent, and thus, the reagent is no longer useful. Meanwhile, in a case where an unused mixed reagent less than the minimum number of times of mixed reagent adjustment is generated, when an analysis of a new sample is requested within a predetermined period of time, the unused mixed reagent can be used. Therefore, it is highly possible to reduce reagent costs in a case of a surplus of the mixed reagent compared to a case of a surplus of the reagent.

Processing of Determining Number of Times of Mixed Reagent Adjustment (Application Example [1])

In the present Embodiment 2, in addition to the number of requested samples, the minimum number of times of mixed reagent adjustment, and the maximum number of times of mixed reagent adjustment, in accordance with the number of remaining reagents, the number (N) of times of mixed reagent adjustment for each mixed reagent preparation cycle is variably determined so that the number of remaining reagents is minimized when the analysis is completed. FIG. 10 is a flow chart illustrating an example of the processing contents applied when determining the number of times of mixed reagent adjustment in the automatic analysis device of Embodiment 2 of the present invention. The automatic analysis device of the present Embodiment 2 has a configuration of FIG. 1 described above. The flow illustrated in FIG. 10 is mainly executed by the analysis plan section 125a inside the control unit 125 of FIG. 1.

The analysis plan section 125a executes the flow of FIG. 10 while monitoring the number (K) of remaining reagents of the reagent (for example, the primer) which is restricted by the dispensing accuracy. In Step 1001, when an analysis of a sample of the number (J) of requested samples is requested, the analysis plan section 125a calculates (the number (K) of remaining reagents–the number (J) of requested samples).

Here, in a case of (the number (K) of remaining reagents–the number (J) of requested samples)≥the minimum number (Nmin) of times of mixed reagent adjustment, when all the analysis of a sample of the number (J) of requested samples is completed, it is possible to maintain the number (K) of remaining reagents≥Nmin. Therefore, there is no need to generate a useless reagent. As indicated in Steps 1002 and 1004, similar to the case of FIG. 4 in Embodiment 1, the analysis plan section 125a executes the processing of calculating Expression (1) by applying the number (J) of requested samples, and the processing of determining the number of times of mixed reagent adjustment in FIG. 5, thereby determining the number (N) of times of mixed reagent adjustment so as to minimize the number of unused mixed reagents.

Meanwhile, in Step 1001, in a case where (the number (K) of remaining reagents–the number (J) of requested samples) <Nmin, when all the analysis of the sample of the number (J) of requested samples is completed, a useless reagent is generated. Therefore, in order to cause the number (K) of remaining reagents to be zero, as indicated in Step 1003, the analysis plan section 125a first calculates the integral quotient Q and the remainder R by applying Expression (2) in which the number (J) of requested samples is replaced by the number (K) of remaining reagents with respect to Expression (1).

$$K/N\max = Q \times N\max + R \quad (2)$$

Thereafter, as indicated in Step 1004, the analysis plan section 125a executes the processing of determining the number of times of mixed reagent adjustment of FIG. 5 by applying the integral quotient Q and the remainder R which are obtained through Expression (2), thereby determining the number (N) of times of mixed reagent adjustment. Accordingly, the number (K) of remaining reagents is minimized by deliberately preparing (K–J) unused mixed reagents.

FIGS. 11 and 12 are explanatory diagrams respectively illustrating specific examples of the numbers of times of mixed reagent adjustment determined in accordance with the number of requested samples, the numbers of unused mixed reagents, and the numbers of remaining reagents, in the flow of FIG. 10. In FIG. 11, similar to the case of FIG. 13(a), in a case where the maximum number (Nmax) of times of mixed reagent adjustment is set to 8, the minimum number (Nmin) of times of mixed reagent adjustment is set to 4, and the number (K) of remaining reagents is set to 8, and in a case where the number of requested samples ranges from 1 to 8, the numbers of times of mixed reagent adjustment, the numbers of remaining reagents, and the numbers of unused mixed reagents are illustrated.

As illustrated in FIG. 11, in a case where the number (J) of requested samples ranges from 1 to 4, the number (N) of times of mixed reagent adjustment is set to 4 which is the minimum number (Nmin) of times of mixed reagent adjustment through Steps 1002 and 1004 of FIG. 10. As a result thereof, the number (K) of remaining reagents ≥4 can be maintained. Therefore, there is no generation of a useless reagent, and in a case where the number (J) of requested samples ranges from 1 to 3, an unused mixed reagent is generated. In addition, in a case where the number (J) of requested samples ranges from 5 to 8, the number (N) of times of mixed reagent adjustment is set to 8 through Steps 1003 and 1004 of FIG. 10. As a result thereof, in a case where the number (J) of requested samples ranges from 5 to 7, being different from the case of FIG. 13(a), it is possible to completely use all the reagents, instead of preparing the unused mixed reagent.

In FIG. 12, similar to the case of FIG. 13(b), in a case where the maximum number (Nmax) of times of mixed reagent adjustment is set to 8, the minimum number (Nmin) of times of mixed reagent adjustment is set to 4, and the number (K) of remaining reagents is set to 10, and in a case where the number of requested samples ranges from 1 to 10, the numbers of times of mixed reagent adjustment, the numbers of remaining reagents, and the numbers of unused mixed reagents are illustrated.

As illustrated in FIG. 12, in a case where the number (J) of requested samples ranges from 1 to 4, the number (N) of times of mixed reagent adjustment is set to 4 which is the minimum number (Nmin) of times of mixed reagent adjustment, through Steps 1002 and 1004 of FIG. 10. As a result thereof, the number (K) of remaining reagents ≥4 can be maintained. Therefore, there is no generation of a useless reagent, and in a case where the number (J) of requested samples ranges from 1 to 3, an unused mixed reagent is generated. In addition, in a case where the numbers (J) of requested samples are 5 and 6, the numbers (N) of times of mixed reagent adjustment are respectively set to 5 and 6 through Steps 1002 and 1004 of FIG. 10. As a result thereof, the number (K) of remaining reagents ≥4 can be maintained, there is no generation of a useless reagent, and no generation of an unused mixed reagent as well.

In addition, in a case where the number (J) of requested samples ranges from 7 to 10, regarding the number (N) of times of mixed reagent adjustment, the first cycle of the mixed reagent preparation cycle is set to 6 and the second cycle is set to 4 through Steps 1003 and 1004 of FIG. 10. As a result thereof, in a case where the number (J) of requested samples ranges from 7 to 9, being different from the case of FIG. 13(b), it is possible to completely use all the reagents, instead of preparing the unused mixed reagent.

Hereinbefore, by applying the automatic analysis device of the present Embodiment 2, based on the number of requested samples, the minimum number of times of mixed reagent adjustment, the maximum number of times of mixed reagent adjustment, and the number of remaining reagents, so as to minimize the number of remaining reagents, it is possible to determine the number of times of preparing the mixed reagent (the number of mixed reagent preparation cycles) and the number of times of mixed reagent adjustment for each cycle. As a result thereof, representatively, it is possible to reduce the reagent which is subjected to being discarded and to reduce the reagent costs. In other words, by prioritizing a surplus of the mixed reagent instead of a surplus of the reagent, there is a case where the reagent costs can be further reduced.

Embodiment 3

Processing of Determining Number of Times of Mixed Reagent Adjustment (Application Example [2])

In the present Embodiment 3, through the methods of Embodiment 1 and Embodiment 2 described above, in a case where an unused mixed reagent is generated, after the unused mixed reagent is prioritized to be used, in accordance with the processing of Embodiment 1 or Embodiment 2, the number of times of mixed reagent adjustment is set.

Specifically, first, in circumstances where an amount of the unused mixed reagent for M analyses (M<Nmin) is present, and in a case where analyses of P samples within a predetermined period of time are requested, the genetic testing device 10 of FIG. 1 first performs processing of M samples by applying the unused mixed reagent. Thereafter, the analysis plan section 125a of FIG. 1 replaces the number (J) of requested samples described in Embodiment 1 or 2 with (P−M), thereby executing the processing of Embodiment 1 or 2 (the flow of FIG. 4 or 10). In addition, in a case where there is no request of an analysis of a sample within a predetermined period of time, the genetic testing device 10 of FIG. 1 discards the unused mixed reagent. Accordingly, it is possible to further minimize the unused mixed reagent and to further reduce the reagent costs.

Embodiment 4

Processing Determining Number of Times of Mixed Reagent Adjustment when Additional Sample is Generated (Application Example [3])

In the present Embodiment 4, through the methods of Embodiment 1 to Embodiment 3 described above, in a case where an additionally requested sample is generated, and in a case where there is the number (J2) of requested samples before the preparation of the mixed reagent, by using the number of requested samples (J4=J2+J3) obtained by adding J2 and the number (J3) of additionally requested samples, in accordance with the processing from Embodiment 1 to Embodiment 3, the number of times of mixed reagent adjustment is set.

FIG. 14 is an explanatory diagram in a case where the flow of FIG. 5 is executed without using Embodiment 4. FIG. 14 illustrates a case where the maximum number (Nmax) of times of mixed reagent adjustment is set to 8, and the minimum number (Nmin) of times of mixed reagent adjustment is set to 4. In Step 1400, in the analysis plan section 125a, analyses of 15 samples are requested. In accordance with the flow of FIG. 5, in Step 1401, the analysis plan section 125a prepares an amount of mixed reagent for 8 times as the first flow of FIG. 3 (that is, the mixed reagent preparation cycle).

Subsequently, between the first mixed reagent preparation cycle in Step 1401 and the second reagent mixed preparation cycle in Step 1403, as Step 1402, analyses of three samples are requested in the analysis plan section 125a. In this case, in a case where an amount of mixed reagent for 7 times is prepared in the second mixed reagent preparation cycle, in Step 1404, with respect to the number of requested samples of the three samples, the analysis plan section 125a prepares an amount of mixed reagent for 4 times which is the minimum number (Nmin) of times of mixed reagent adjustment, as the number (N) of times of mixed reagent adjustment. Therefore, the number of remaining reagents=1 is generated.

FIG. 15 is an explanatory diagram in a case where the flow of FIG. 5 is executed by using Embodiment 4. FIG. 15 illustrates a case where the maximum number (Nmax) of times of mixed reagent adjustment is set to 8, and the minimum number (Nmin) of times of mixed reagent adjustment is set to 4. In Step 1500, in the analysis plan section 125a, analyses of 15 samples are requested. In accordance with the flow of FIG. 5, in Step 1501, the analysis plan section 125a prepares an amount of mixed reagent for 8 times as the first flow of FIG. 3 (that is, the mixed reagent preparation cycle).

Subsequently, between the first mixed reagent preparation cycle in Step 1501 and the second reagent mixed preparation cycle in Step 1503, as Step 1502, analyses of three samples are requested in the analysis plan section 125a. Here, the analysis plan section 125a resets the number of times of mixed reagent preparation by using the number of requested samples (J4=J2+J3), that is, J4=10 samples obtained by adding 7 samples which is the number (J2) of requested samples before the preparation of the mixed reagent and three samples which is the number (J3) of additionally requested samples. In this manner, it is possible to prepare an amount of mixed reagent for 6 times in Step 1503, and to prepare an amount of mixed reagent for 4 times in Step 1504, and thus, the unused mixed reagent can be zero.

In addition, in a case where the number (J) of requested samples indicates 15 samples and the number of additionally requested samples indicates 9 samples, and in a case where Embodiment 4 is not used, in the flow of FIG. 3 (that is, the mixed reagent preparation cycle), the analysis plan section 125a executes four mixed reagent preparation cycles in total, thereby causing the unused mixed reagent to be zero. Specifically, with respect to the 15 samples of the number of requested samples, two mixed reagent adjustment cycles are executed, and amounts of mixed reagent for eight times and seven times are respectively prepared. Subsequently, with respect to the 9 samples of the number of additionally requested samples, two mixed reagent adjustment cycles are executed, and amounts of mixed reagent for five times and four times are respectively prepared.

Meanwhile, in a case where Embodiment 4 is used, the analysis plan section 125a executes three mixed reagent preparation cycles in total, thereby causing the unused mixed reagent to be zero. Specifically, with respect to the 15 samples of the number of requested samples, first, the first mixed reagent adjustment cycle is executed, and an amount of mixed reagent for 8 times is prepared. Subsequently, with respect to 16 samples which is the number (J4) of requested samples obtained by adding 7 samples which is the number (J2) of requested samples before the preparation of the mixed reagent and 8 samples which is the number (J3) of additionally requested samples, two mixed reagent adjustment cycles are executed, thereby respectively preparing amounts of mixed reagent for 8 times and another 8 times. In this manner, by using the present Embodiment 4, it is possible to reduce the number of mixed reagent preparation cycles.

Hereinbefore, by applying the automatic analysis device of the present Embodiment 4, in a case where an additionally requested sample is generated, based on the number of requested samples before the preparation of the mixed reagent, the number of additionally requested samples, the minimum number of times of mixed reagent adjustment, and the maximum number of times of mixed reagent adjustment, so as to minimize the number of remaining reagents, it is possible to determine the number of times of preparing the mixed reagent (the number of mixed reagent preparation cycles) and the number of times of mixed reagent adjustment for each cycle. As a result thereof, representatively, it is possible to reduce the unused mixed reagent which is subjected to being discarded and to reduce the reagent costs. In addition, by adding the requested numbers, it is possible to reduce the number of mixed reagent preparation cycles and to improve the throughput of the device.

Hereinbefore, the invention made by the inventor has been described in detail based on the embodiments. However, the present invention is not limited to the above-described embodiments and various changes can be made without departing from the gist thereof. For example, the above-described embodiments are described in detail in order to make the present invention easy to understand. Therefore, the invention is not necessarily limited to the embodiment including all the described configurations. In addition, the configuration of a certain embodiment can be partially replaced by the configuration of a different embodiment, and the configuration of a certain embodiment can be added to the configuration of a different embodiment. In addition, a portion of the configuration of each embodiment can be subjected to addition, deletion, and replacement of a different configuration.

For example, here, description has been given regarding an example of the genetic testing device. However, the invention is not necessarily limited thereto. As long as the automatic analysis device uses the mixed reagent, a similar effect can be obtained by performing similar application.

REFERENCE SIGNS LIST

10 GENETIC TESTING DEVICE
100 TEST UNIT
101 SAMPLE VESSEL
102 SAMPLE VESSEL RACK
103 REAGENT VESSEL
104 REAGENT VESSEL RACK
105 MIXED REAGENT ADJUSTMENT VESSEL
106 MIXED REAGENT ADJUSTMENT VESSEL RACK
107 REACTOR VESSEL
108 REACTOR VESSEL RACK
109 REACTION LIQUID ADJUSTMENT POSITION
110 CLOSING UNIT
111 AGITATION UNIT
112, 114 DISPENSING CHIP
113, 115 DISPENSING CHIP RACK
116 ROBOT ARM X-SHAFT
117 ROBOT ARM Y-SHAFT
118 ROBOT ARM DEVICE
119 GRIPPER UNIT
120 DISPENSING UNIT
121 NUCLEIC ACID AMPLIFICATION UNIT
122 DISCARD BOX
123 INPUT UNIT
124 DISPLAY UNIT
125 CONTROL UNIT
125a ANALYSIS PLAN SECTION
125b ANALYSIS EXECUTION SECTION
125c DATA PROCESSING SECTION

The invention claimed is:

1. An automatic analysis device comprising:
a reaction mixture that includes a plurality of reagents that are mixed together into a mixed reagent;
reactor vessels;
a dispensing unit that prepares an amount of the mixed reagent needed to conduct a given number of analyses;
a display unit; and
a control unit that is configured to set the amount of the mixed reagent to be prepared to a range between a maximum value and a minimum value when a number of analyses requested by a user exceeds the given number of analyses, so as to minimize a surplus of the mixed reagent, wherein
the dispensing unit collectively prepares an amount of the mixed reagent for N analyses for each time mixed reagents are prepared (mixed reagent preparation cycles),
the control unit sets a value of N for each of the mixed reagent preparation cycles within a range from Nmin to Nmax in a case where Nmin which is a minimum value of the value of N and Nmax which is a maximum value thereof are stored in a memory of the automatic analysis device and analyses of J samples are requested while an amount of sample for one analysis is considered to be one sample, and sets the value of N for each of the mixed reagent preparation cycles to any one in a range of Nmax≥N≥Nmin so as to minimize the surplus of the mixed reagent after the analyses of the J samples are completed, the dispensing unit is configured to dispense one sample and an amount of mixed reagent for one analysis in the amount of the mixed reagent for N analyses into each of the reactor vessels, the dispensing unit is configured to perform dispensing processing based on the calculation result by the control unit, and the control unit executes the mixed reagent preparation cycle that is set through first processing in which Q that is an integral quotient and R that is a remainder are calculated by applying (J/Nmax=Q×Nmax+R), and second processing in which the value of N is set to Nmin in a first cycle that is a cycle of the mixed reagent preparation cycles and the value of N is set to (Nmax+R−Nmin) in a second cycle that is another cycle thereof in a case of a first condition of Q≥1 and 0<R<Nmin;

the dispensing unit has a dispensing accuracy guarantee range, and the given number of analyses is set based on a lower limit of the dispensing accuracy guarantee range of the dispensing unit, and a fluorescence detection mechanism that performs fluorescence detection on the mixed reagent in the reactor vessels, wherein the control unit manages the fluorescence detection in the reactor vessels, and outputs a signal to the display unit to display the detection results.

2. The automatic analysis device according to claim 1, wherein the control unit sets the mixed reagent preparation cycle to (Q+1) times.

3. The automatic analysis device according to claim 2, wherein the control unit sets the value of N to Nmax in a cycle excluding the first and second cycles of the (Q+1) mixed reagent preparation cycles under the first condition of the second processing in a case of Q≥2.

4. The automatic analysis device according to claim 3, wherein in the second processing, the control unit further sets the value of N to Nmin in a case of a second condition of Q=0 and R<Nmin, sets the value of N to R in a case of a third condition of Q=0 and R≥Nmin, sets the value of N to R in a third cycle that is a cycle of the (Q+1) mixed reagent preparation cycles in a case of a fourth condition of Q≥1 and R≥Nmin or Q≥1 and R=0, and sets the value of N to Nmax in a cycle excluding the third cycle.

5. The automatic analysis device according to claim 2, wherein in a case of the first condition, instead of the second processing, the control unit sets the value of N to Nmin in all the mixed reagent preparation cycles in a case of a fifth condition of ((Q+1)×Nmin)≥J, and wherein in a case of a sixth condition of ((Q+1)×Nmin)<J, in a repetitive number ith mixed reagent preparation cycle, the control unit sets the value of N to Nmax in a cycle of the (Q+1) mixed reagent preparation cycles in a case of a seventh condition of (i×Nmax)+(Q−i+1)×Nmin≤J, sets the value of N to J−(i−1)×Nmax−(Q−i+1)×Nmin in a cycle that is a cycle of the mixed reagent preparation cycles excluding the seventh condition from (Q+1) times in a case of an eighth condition of (i×Nmax)+(Q−i+1)×Nmin>J, and sets the value of N to Nmin in a cycle excluding the eighth condition.

6. The automatic analysis device according to claim 1, wherein the control unit monitors K indicating an amount for a remaining number of times of analyses which remain while having a reagent of the plurality of reagents as a target, calculates (K−J) in a case where analyses of the J samples are requested, executes the first and second processing in a case of (K−J)≥Nmin, calculates Q that is the integral quotient and R that is the remainder by applying (K/Nmax=Q×Nmax+R) instead of the first processing in a case of (K−J)<Nmin, and executes the mixed reagent preparation cycle which is set through the second processing by applying the Q and the R.

7. The automatic analysis device according to claim 1, wherein the automatic analysis device analyzes the sample by applying an amount of mixed reagent for M analyses after the analyses of the J samples are completed in a case where there is a surplus of the mixed reagent for M analyses (M<Nmin) and in a case where a request of an analysis of a sample is newly generated within a predetermined period of time.

8. The automatic analysis device according to claim 6, wherein the control unit notifies a user of a fact that there is a surplus of an amount of the mixed reagent for analyses less than Nmin in a case of a condition which corresponds a second condition of the second processing.

9. The automatic analysis device according to claim 1, wherein in a case where an additionally requested sample is generated, by applying the number (J4=J2+J3) of requested samples obtained by adding the number (J2) of requested samples before preparation of the mixed reagent and the number (J3) of additionally requested samples, instead of the first processing, Q that is the integral quotient and R that is the remainder are calculated by applying (J4/Nmax=Q×Nmax+R), and the mixed reagent preparation cycle set through the second processing by applying the Q and the R is executed.

10. The automatic analysis device according to claim 1, wherein the automatic analysis device is a genetic test device.

* * * * *